(12) United States Patent
Taylor et al.

(10) Patent No.: US 10,363,380 B2
(45) Date of Patent: Jul. 30, 2019

(54) DEVICE AND METHODS FOR LIFTING PATIENT TISSUE DURING LAPAROSCOPIC SURGERY

(71) Applicant: Lapovations, LLC, Fayetteville, AR (US)

(72) Inventors: Chris Taylor, Harrison, AR (US); Jared Greer, Fayetteville, AR (US); Abby Terluow, Fayetteville, AR (US); Kinan Alhallak, Paragould, AR (US); Christopher Oldfield, Benton, AR (US); Mason Harper, Fayetteville, AR (US); Patrick O'Brien, Fayetteville, AR (US); Jill Goodrich, Fayetteville, TN (US); Terry Oquin, Fairhope, AL (US); Byron Smith, Nashville, TN (US)

(73) Assignee: Lapovations, LLC, Fayetteville, AR (US)

( * ) Notice: Subject to any disclaimer, the term of this patent is extended or adjusted under 35 U.S.C. 154(b) by 0 days.

(21) Appl. No.: 15/601,941

(22) Filed: May 22, 2017

(65) Prior Publication Data
US 2017/0333643 A1 Nov. 23, 2017

Related U.S. Application Data

(60) Provisional application No. 62/339,424, filed on May 20, 2016.

(51) Int. Cl.
*A61M 5/42* (2006.01)
*A61M 1/00* (2006.01)
(Continued)

(52) U.S. Cl.
CPC ......... *A61M 5/425* (2013.01); *A61B 17/0281* (2013.01); *A61B 17/34* (2013.01);
(Continued)

(58) Field of Classification Search
CPC .................................................. A61B 17/0281
See application file for complete search history.

(56) References Cited

U.S. PATENT DOCUMENTS 4,892,517 A * 1/1990 Yuan .................. A61M 1/0023
604/74
5,224,947 A 7/1993 Cooper et al.
(Continued)

FOREIGN PATENT DOCUMENTS

CN 202960684 U 6/2013
CN 203953814 U 11/2014
(Continued)

OTHER PUBLICATIONS

Böhm, B., M. Knigge, M. Kraft, K. Gründel, and U. Boenick. "Influence of Different Trocar Tips on Abdominal Wall Penetration during Laparoscopy." Surgical Endoscopy 12, No. 12 (Jun. 30, 1998): 1434-438. doi:10.1007/s004649900876.
(Continued)

*Primary Examiner* — Nicholas W Woodall
(74) *Attorney, Agent, or Firm* — Waller Lansden Dortch & Davis, LLP; Matthew C. Cox

(57) ABSTRACT

A surgical device that provides a suction force against a patient's body. The device includes a handle and a suction head pivotally attached to the handle. The suction head includes an open-ended suction chamber having a rim positioned to engage the patient's skin. An actuator on the handle operates a pump to draw a negative pressure in the suction chamber, causing the rim to seal against the patient's skin via the suction force. Once the suction force is initiated, the user may lift the handle away from the patient's body to lift tissue. The lifted tissue provides a site for insertion of a trocar or Veress needle for a laparoscopic procedure in some embodiments. A gimbal disposed between the handle and the suction head provides at least two degrees of freedom (Continued)

such that the handle can be rotated and pivoted to optimize the direction of applied lifting force.

15 Claims, 12 Drawing Sheets

(51) Int. Cl.
*A61B 17/34* (2006.01)
*A61B 17/02* (2006.01)
*A61B 17/30* (2006.01)

(52) U.S. Cl.
CPC ....... *A61B 17/3498* (2013.01); *A61M 1/0068* (2014.02); *A61M 1/0092* (2014.02); *A61B 2017/306* (2013.01); *A61M 2205/3331* (2013.01)

(56) References Cited

U.S. PATENT DOCUMENTS

| | | | |
|---|---|---|---|
| 5,281,229 A | 1/1994 | Neward | |
| 5,336,158 A * | 8/1994 | Huggins | A61H 9/005 601/14 |
| 5,353,785 A | 10/1994 | Wilk | |
| 5,395,379 A * | 3/1995 | Deutchman | A61B 10/0283 604/227 |
| 5,545,123 A | 8/1996 | Ortiz et al. | |
| 5,865,730 A | 2/1999 | Fox et al. | |
| 5,865,827 A | 2/1999 | Bullister | |
| 6,042,539 A | 3/2000 | Harper et al. | |
| 6,059,795 A | 5/2000 | Wallace et al. | |
| 6,074,399 A | 6/2000 | Wallace et al. | |
| 6,355,047 B1 | 3/2002 | Wallace et al. | |
| 7,234,743 B2 * | 6/2007 | Robinson | H01J 9/003 294/184 |
| 7,585,281 B2 | 9/2009 | Nezhat et al. | |
| 7,992,908 B2 * | 8/2011 | Finck | F16B 47/00 248/205.8 |
| 9,050,133 B1 | 6/2015 | Boone, III et al. | |
| 2005/0010197 A1 | 1/2005 | Lau et al. | |
| 2005/0203334 A1 | 9/2005 | Lonky et al. | |
| 2007/0270745 A1* | 11/2007 | Nezhat | A61B 5/6834 604/115 |
| 2008/0058851 A1 | 3/2008 | Edelstein et al. | |
| 2010/0249755 A1 | 9/2010 | Zappala | |
| 2013/0197315 A1 | 8/2013 | Foley | |
| 2017/0333643 A1 | 11/2017 | Taylor et al. | |

FOREIGN PATENT DOCUMENTS

| | | |
|---|---|---|
| CN | 203988534 U | 12/2014 |
| CN | 107335103 A | 11/2017 |
| WO | 02088546 A1 | 11/2002 |
| WO | 2014125434 A1 | 8/2014 |

OTHER PUBLICATIONS

Corson, Stephen L., MD, Frances R. Batzer, MD, Benjamin Gocial, MD, and Greg Maislin, MS. "Measurement of the Force Necessary for Laparoscopic Trocar Entry." The Journal of Reproductive Medicine 34, No. 4 (Apr. 1989): 282-84.

Fuller, Janie, DDS, Walter Scott, Ph.D., Binita Ashar, MD, and Julia Corrado, MD. "Laparoscopic Trocar Injuries: A Report from a U.S. Food and Drug Administration (FDA) Center for Devices and Radiological Health (CDRH) Systematic Technology Assessment of Medical Products (STAMP) Committee: FDA Safety Communication." U.S. Food and Drug Administration. Nov. 7, 2003. http://www.fda.gov/MedicalDevices/Safety/AlertsandNotices/ucm197339.htm.

Inan, A., M. Sen, C. Dener, and M. Bozer. "Comparison of Direct Trocar and Veress Needle Insertion in the Performance of Pneumoperitoneum in Laparoscopic Cholecystectomy." Acta Chirurgica Belgica 105, No. 5 (2005): 515-18. doi:10.1080/00015458.2005.11679771.

La Chapelle, Claire F., Willem A. Bemelman, Bart MP Rademaker, Teus A. Van Barneveld, and Frank W. Jansen. "A Multidisciplinary Evidence-based Guideline for Minimally Invasive Surgery." Journal of Gynecological Surgery 9 (Jan. 24, 2012): 271-82. doi:10.1007/s10397-012-0731-y.

Toro, Adriana, Maurizio Mannino, Giovanni Cappello, Andrea Di Stefano, and Isidoro Di Carlo. "Comparison of Two Entry Methods for Laparoscopic Port Entry: Technical Point of View." Diagnostic and Therapeutic Endoscopy 2012 (Apr. 5, 2012): 1-7. doi:10.1155/2012/305428.

Vilos, George A., MD, Artin Ternamian, MD, Jeffrey Dempster, MD, and Philippe Y. Laberge, MD. "Laparoscopic Entry: A Review of Techniques, Technologies, and Complications." Journal of Obstetrics and Gynaecology Canada 193 (May 2007): 433-47; http://sogc.org/wp-content/uploads/2013/01/gui193ECPG0705wDisclaimer.pdf.

Lapdome by Dome; Laparoscopic Surgery, Laparoscopic Market Dynamics; domemedical.com/laparoscopic-surgery/ (accessed Jul. 2016), four pages.

strategyr.com/pressMCP-6143.asp (accessed Jul. 2016).

Laparoscopic Devices Market—Global Industry Analysis, Size and Forecast, 2015-2025; http://www.futuremarketinsights.com/reports/laparoscopic-devices-market (accessed Jul. 2016), four pages.

International Search Report and Written Opinion for PCT/US2017/033887, received Aug. 15, 2017, 14 pages.

PCT/US2018/065014 International Search Report and Written Opinion, dated Mar. 28, 2019, 13 pages.

* cited by examiner

DEVICE AND METHODS FOR LIFTING PATIENT TISSUE DURING LAPAROSCOPIC SURGERY

CROSS-REFERENCE TO RELATED APPLICATION

This application claims priority to and benefit of U.S. Provisional Patent Application No. 62/339,424 entitled "Surgical Device," all of which is hereby incorporated by reference in its entirety.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable.

REFERENCE TO SEQUENCE LISTING OR COMPUTER PROGRAM LISTING APPENDIX

Not Applicable.

BACKGROUND

The present disclosure relates generally to surgical devices and more particularly to a device and methods for lifting tissue of a patient prior to insertion of a surgical instrument such as a trocar or Veress needle.

During various surgical procedures, including laparoscopy, surgical instruments such as a trocar, Veress needle or access port may be inserted into the tissue of a human or animal. In some procedures, the instrument is inserted in a position to access the abdominal cavity. The initial surgical instrument or trocar is preferably placed through the umbilicus because the abdominal wall is at its thinnest in this region. A laparoscopic camera is then placed through this initial trocar to aid in visualizing the intraabdominal cavity and the structures therein. Carbon dioxide gas is then used to insufflate the abdominal cavity, thereby creating a pneumoperitoneum or space to operate. Once the pneumoperitoneum is created, secondary trocars can be placed under direct visualization utilizing the laparoscopic camera thus reducing the risk of injury.

Patient injuries most often occur during initial placement of the trocar or Veress needle, which is generally considered to be the most dangerous portion of a laparoscopic surgery. Currently, there are two common methods for the placement of the primary umbilical trocar: the blind technique and the open (Hasson) technique.

The blind technique can be accomplished either before or after the creation of the pneumoperitoneum. Some surgeons prefer insufflating the abdominal cavity prior to the placement of the initial trocar. This is accomplished with the use of a Veress needle. The needle is blindly introduced through an umbilical incision. Carbon dioxide gas is introduced through the Veress needle, elevating the abdominal wall away from the underlying structures. The Veress needle is then removed, and the primary trocar placed.

Other surgeons prefer placing the primary trocar prior to insufflating the abdomen. This is the direct entry method and is performed using a technique called a "controlled jab." The trocar is placed through an umbilical incision under controlled force using a stabbing motion with care not to penetrate beyond the abdominal wall. Most surgeons elevate the abdominal wall during blind insertion of either the primary trocar or the Veress needle. This reduces the risk of injury to underlying structures.

The most common type of injury is to vascular structures, bowel, or to other visceral organs. Multiple studies have shown that complication rates are similar between the Veress needle and direct entry as well as between the blind technique and the open Hasson technique. Various techniques and inventions have been described to assist with elevation of the abdominal wall to facilitate blind trocar or Veress needle placement. This includes rarely used devices such as retractors and lifting rods used to mechanically elevate the abdominal wall thereby creating negative pressure within the abdomen allowing a space for initial trocar placement or room to operate without the need for creating a pneumoperitoneum.

More commonly, two conventional manual techniques for lifting the abdominal wall are utilized. The first method involves grasping and lifting the abdominal wall below or on either side of the umbilicus with one's hand. The second method utilizes perforating towel clips placed in a similar location to provide a handle on which to lift and elevate the abdominal wall. Each of these techniques require that sufficient elevation of the abdominal wall is maintained in opposition to the downward force generated during primary trocar or Veress needle placement. Although providing a more secure grasp of the abdominal wall, towel clips pierce the abdominal skin and therefore risk injury and trauma to vessels and tissue. This is also a source of postoperative discomfort to what is intended to be a minimally invasive procedure. Grasping and lifting the abdominal wall by hand poses its own challenges. Whether the surgeon is lifting the abdomen below the umbilicus or the surgeon and his assistant are lifting on either side of the umbilicus, it can be difficult to maintain a grip and the proper elevation to insure inadvertent injury does not occur to the underlying structures. The shape, elasticity and overall thickness of the abdominal wall can also prohibit one from adequately grasping the abdomen by hand. Also, lifting the full thickness of the abdominal wall by hand risks inadvertently grasping and elevating the omentum and other underlying structures together with the abdominal wall bringing these structures into the path of the trocar or Veress needle.

In an effort to improve on current tools and techniques, a number of devices have been developed. One recent apparatus, marketed under the name of LapDome by Narbitas, utilizes a dome shaped device and negative pressure generated from external operating room suction to raise the abdominal wall within the dome thereby creating intraabdominal space. A Veress needle is then introduced through the dome and into the elevated abdominal cavity. The abdominal cavity is then insufflated with carbon dioxide gas, and the surgery can commence as usual.

There are several drawbacks to using the LapDome and similar devices. First, it is a bulky apparatus fixated over the abdomen and umbilicus and requires external suction to create lift within the device. Second, the LapDome can be used only with the Veress needle technique and therefore limits a surgeon to a technique that he or she may not be comfortable with performing.

What is needed then are improvements to devices and methods for laparoscopic surgery, and particularly for manipulating and lifting patient tissue for insertion and placement of a surgical device during a surgical procedure, such as but not limited to a trocar or Veress needle.

BRIEF SUMMARY

This Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

One aspect of some embodiments of the present disclosure is a surgical device including a handle and a suction head attached to the handle at a pivotable joint. The joint allows relative angular motion between the suction head and the handle in at least one angular degree of freedom. A manual pump is disposed on the handle, and an actuator is coupled to the pump. A user may manipulate the actuator to operate the pump, thereby creating a suction force between the suction head and the skin of a patient. Once a suction force is established between the suction head and the patient, the user may then lift the surgical device away from the patient's body to lift tissue for trocar insertion.

Another aspect of some embodiments of the present disclosure provides a surgical device including a handle and a suction head attached to the handle at an articulating joint. A gimbal device is positioned at the joint between the suction head and the handle in some embodiments. The gimbal provides a first angular degree of freedom between the gimbal and the handle, and a second angular degree of freedom between the gimbal and the suction head. Thus, the gimbal operates as an intermediate structure between the handle and the suction head to allow relative angular movement between the handle and the suction head in at least two degrees of freedom.

A further aspect of some embodiments of the present disclosure provides a surgical device including a handle and a suction head, wherein a negative pressure suction force may be easily released by manual operation of a pressure release on the suction head.

Another object of some embodiments of the present disclosure is to provide a device and associated methods to lift tissue prior to trocar or Veress needle insertion to allow surgeons to utilize either trocar insertion method.

Another object of some embodiments of the present disclosure is to provide a surgical device for lifting a patient's tissue for insertion of a surgical instrument such as a trocar, wherein the device allows the user to move an actuator in the same direction as the axial pull force for lifting the tissue.

Numerous other objects, advantages and features of the present disclosure will be readily apparent to those of skill in the art upon a review of the following drawings and description of a preferred embodiment.

DETAILED DESCRIPTION

Figure 1:
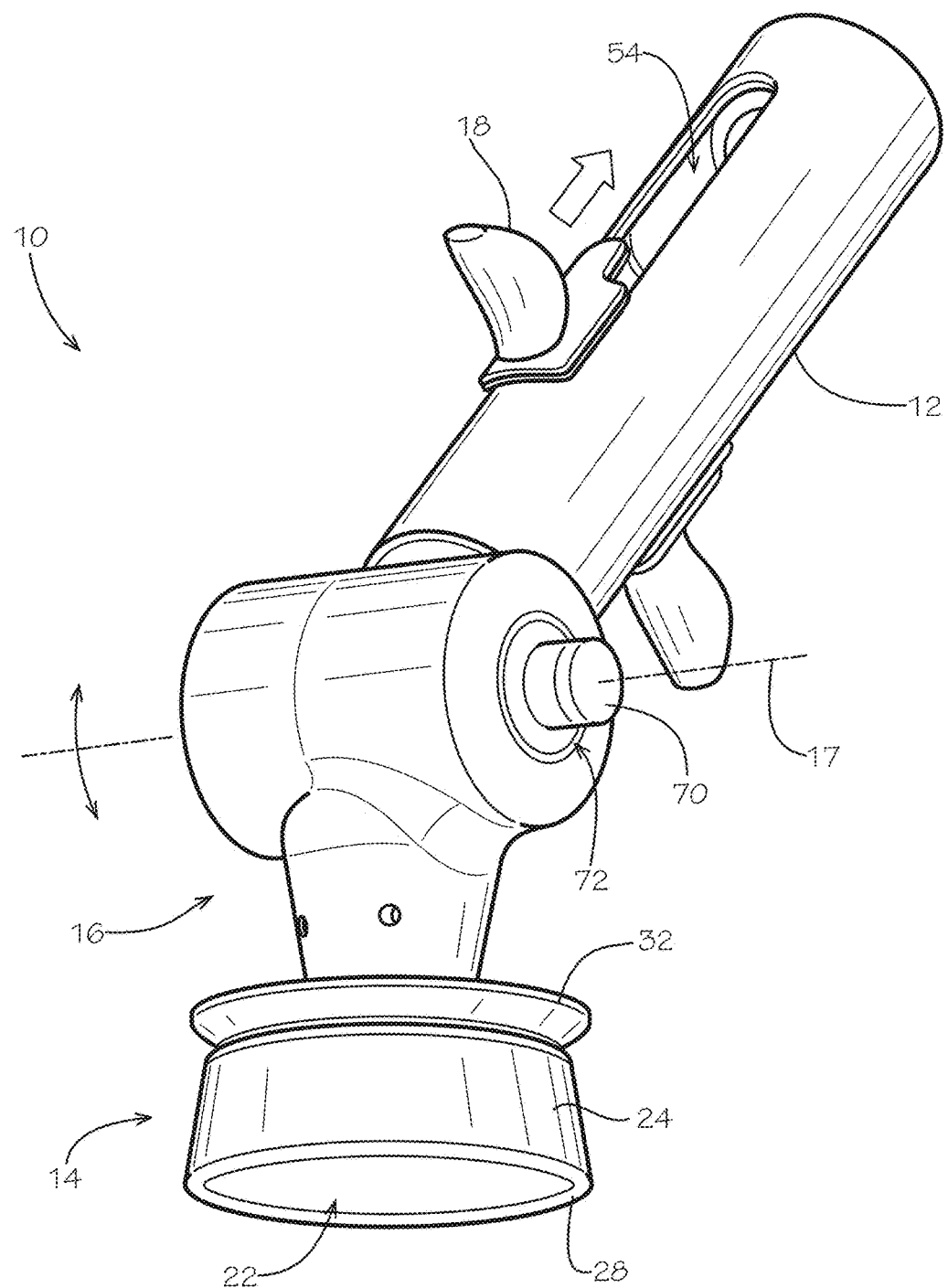
FIG. 1 is a perspective view of an embodiment of a surgical device in accordance with the present disclosure.

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention. Those of ordinary skill in the art will recognize numerous equivalents to the specific apparatus and methods described herein. Such equivalents are considered to be within the scope of this invention and are covered by the claims.

In the drawings, not all reference numbers are included in each drawing, for the sake of clarity. In addition, positional terms such as "upper," "lower," "side," "top," "bottom," etc. refer to the apparatus when in the orientation shown in the drawing, or as otherwise described. A person of skill in the art will recognize that the apparatus can assume different orientations when in use.

Referring to FIG. 1, an embodiment of a surgical device 10 is shown in a perspective view. Device 10 includes a handle 12 and a suction head 14. Handle 12 is attached to suction head 14 at a moveable joint 16. During use, a user may grasp handle 12 while suction head 14 engages a patient's body. Suction head 14 includes a suction cup 24 having an open suction chamber 22. A rim 28 is positioned to engage a patient's body. An actuator 18 on handle 12 is coupled to a pump mechanism housed within the device. When rim 28 is positioned against a patient's body, actuator 18 is manipulated to cause the pump mechanism to draw a negative pressure between the patient's body and the suction head 14. Rim 28 operates as a seal between the patient's skin and the suction head 14. Once a negative pressure suction force is established between the device 10 and the patient via the suction head 14, the user may then use handle 12 to manually lift the patient's tissue while maintaining a negative pressure seal between the patient's body and the rim 28. Once the tissue is lifted, the user may then insert a trocar or Veress needle using any suitable insertion technique.

Figure 3:
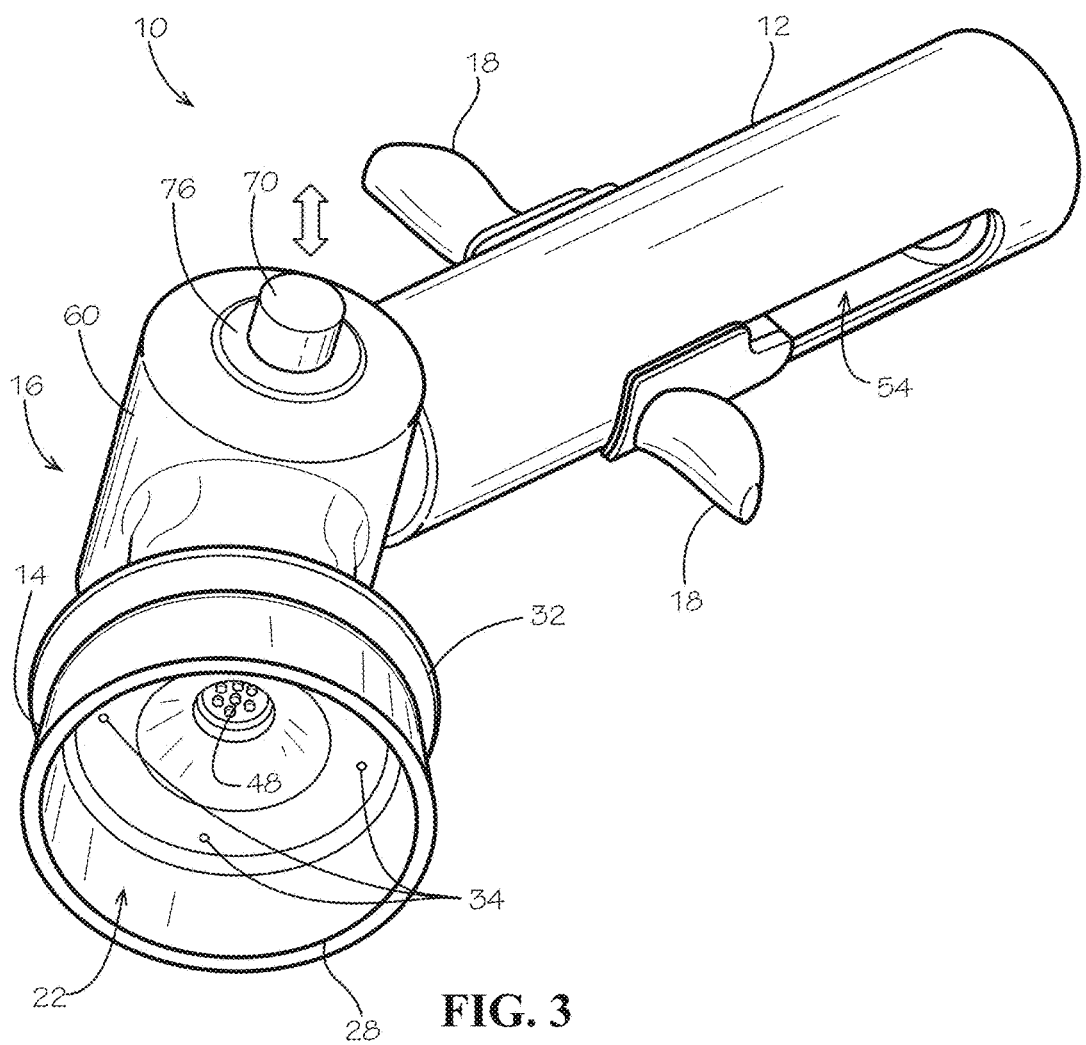
FIG. 3 is a perspective view of an embodiment of a surgical device in accordance with the present disclosure.

After the surgical instrument is inserted, the negative pressure suction force is released by operation of a pressure release 32 on the device 10. One or more pressure release ports 34, shown in FIG. 3, are defined in suction head 14 in some embodiments. Each pressure release port 34 passes through the suction head 14 to allow gas transfer across suction head 14. When a negative pressure is pulled in suction chamber 22, pressure release 32 is held down against the exterior of suction head 14, thereby blocking entry of gas into the suction chamber. In such embodiments, the pressure release 32 is closed. An upturned edge around the perimeter of pressure release 32 provides a location for a user to manually lift the pressure release 32. When pressure release 32 is lifted away from suction head 14, one or more pressure release ports 34 are opened and the suction force created in suction chamber 22 is released as air enters suction chamber 22 quickly through the pressure release ports 34. The pressure release 32 provides a convenient way for a user to quickly release the suction of the device against a patient during an operation.

Figure 2:
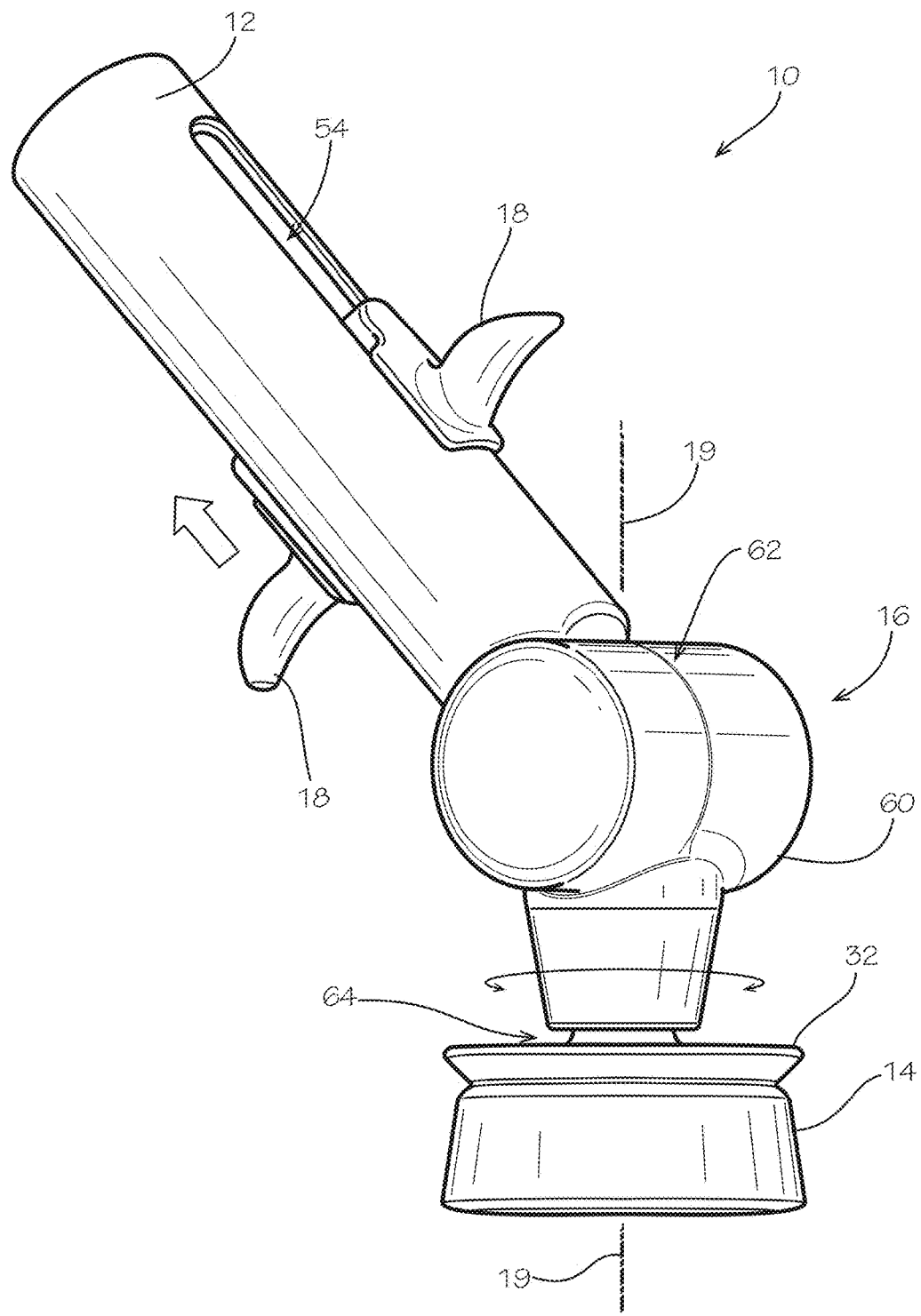
FIG. 2 is a perspective view of an embodiment of a surgical device in accordance with the present disclosure.

Referring to FIG. 1 and FIG. 2, in some embodiments, device 10 includes a joint 16 between handle 12 and suction head 14. Joint 16 provides a first angular degree of freedom about a reference horizontal axis 17. This first angular degree of freedom allows handle 12 to pivot toward and away from the patient's body when in use. The first angular degree of freedom also allows a user to angle the handle relative to suction head 14 for applying a pulling force in various directions away from the patient's body. Notably, the degree of freedom offered by joint 16 in some embodiments, and the at least two degrees of freedom offered by joint 16 in additional embodiments, provide a user with the ability to lift the patient tissue at various angles of application of lifting force. This further allows a user to properly position the user's hands out of the way of the trocar insertion or Veress needle insertion during the laparoscopic surgical procedure using device 10.

As further seen in FIG. 2, in additional embodiments, device 10 includes a joint 16 between handle 12 and suction head 14 that provides a second angular degree of freedom about a reference vertical axis 19. The second angular degree of freedom allows a user to pivot the handle relative to the suction head 14 when the suction head 14 is engaged with the patient's body. For example, during use, a user may press suction head 14 against a patient's body. Then, the user may manipulate actuator 18 along travel slot 54 to draw a negative pressure suction force between suction head 14 and the patient's body. Once the suction force is established, the user may then pivot handle 12 relative to suction head 14 about vertical axis 19 via joint 16. In such embodiments, joint 16 may be referred to as having two degrees of freedom—a first degree of freedom about reference axis 17, shown in FIG. 1, and a second degree of freedom about reference axis 19, shown in FIG. 2.

Alternatively, in some embodiments, joint 16 includes only the first degree of freedom about reference axis 17. In further embodiments, joint 16 includes only the second degree of freedom about reference axis 19.

During use, a negative pressure suction force is established in suction head 14 using a pump mechanism. Negative pressure is established in suction head 14 using a suction port 48 in fluid communication with the pump mechanism. Suction port 48, shown in FIG. 3, provides one or more orifices in suction head 14 that are open on one side to suction chamber 22 and are open on the other side to the pump mechanism 90, shown in FIG. 4.

Figure 4:
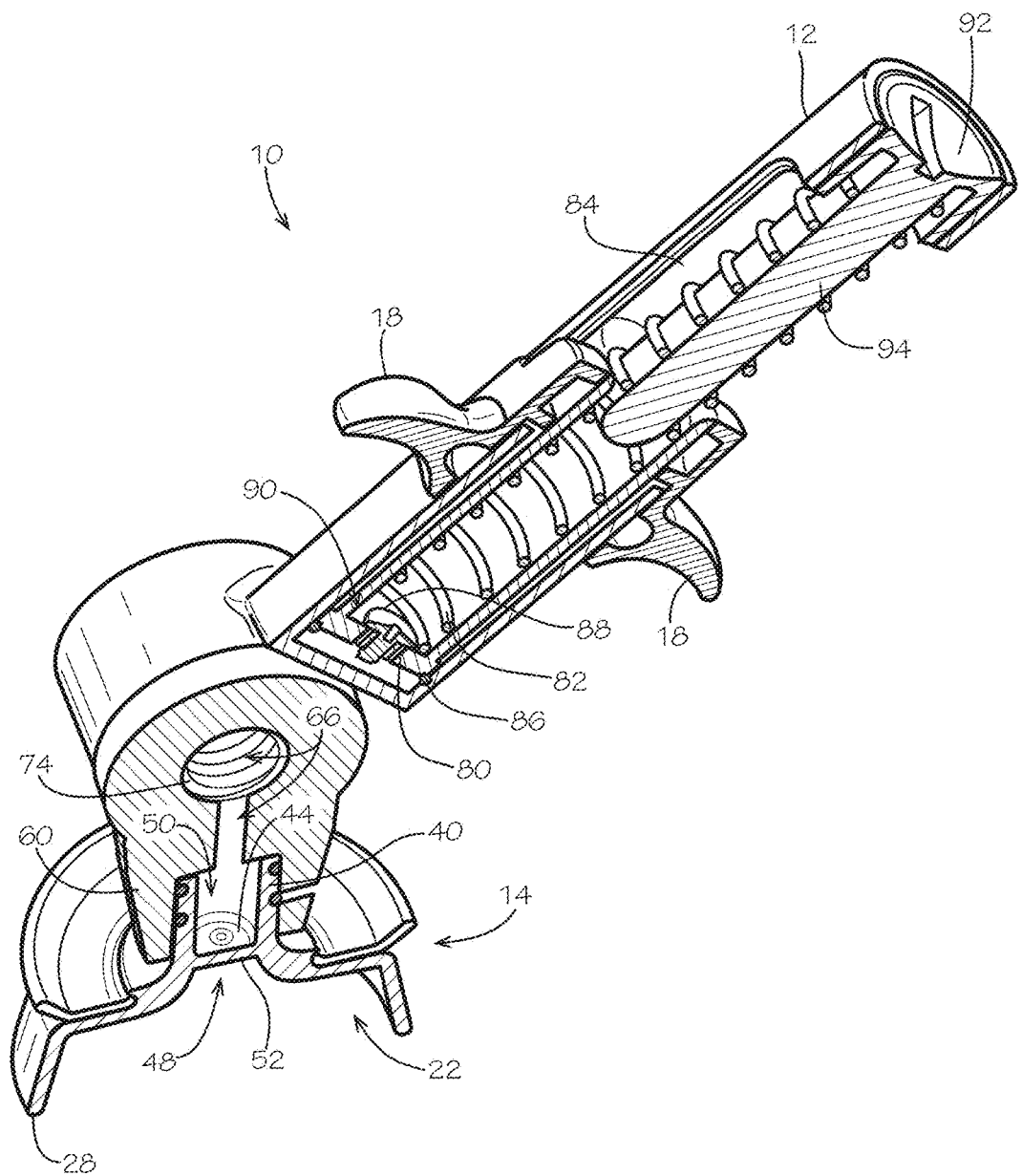
FIG. 4 is a perspective partial cross-sectional view of an embodiment of a surgical device in accordance with the present disclosure.

A suction valve 44 is disposed in suction head 14 to seal suction chamber 22 with a negative applied pressure in some embodiments. Suction valve 44 includes any suitable valve for drawing and holding a reduced pressure in suction chamber 22 via suction port 48. For example, as seen in FIG. 4, an embodiment of a suction valve 44 in suction head 14 includes an umbrella valve positioned above suction port 48. The valve operates as a check valve, allowing negative pressure to be drawn from suction chamber 22 while preventing the flow of gas back into suction chamber 22 when rim 28 is sealed against a patient's body.

Suction valve 44 is seated in a stem 40 on suction head 14 in some embodiments, as seen in FIG. 4. Stem 40 includes a protruding structure extending upwardly from the suction head 14 allowing attachment to joint 16. Stem 40 includes a hollow interior stem channel 50, and a stem wall 52 spanning the stem channel 50. Stem wall 52 forms a separation between suction chamber 22 and stem channel 50. One or more suction ports 48 are defined in stem wall 52, and suction valve 44 is seated in stem channel 50 on stem wall 52 in some embodiments. During use, when a negative pressure is drawn on suction head 14 via stem channel 50, suction valve 44 opens slightly to allow the negative pressure to act on suction chamber 22 via suction ports 48, thereby drawing a corresponding negative pressure on suction chamber 22. When the desired negative pressure is reached, suction valve 44 presses back down against stem wall 52 thereby blocking suction ports 48 and maintaining the reduced pressure in suction chamber 22.

In some embodiments, a gimbal 60 provides joint 16 between handle 12 and suction head 14. Gimbal 60 includes an intermediate structure located between handle 12 and suction head 14 to provide two angular degrees of freedom between handle 12 and suction head 14. Gimbal 60 includes a first pivoting gimbal joint 62 between gimbal 60 and handle 12, shown in FIG. 2. First gimbal joint 62 allows handle 12 to pivot about a reference horizontal axis 17, as seen in FIG. 1. First gimbal joint 62 includes a first gimbal joint seal between gimbal 60 and handle 12. The first gimbal joint seal may include any suitable seal for maintaining a pressure-tight seal along first gimbal joint 62 during articulation between handle 12 and gimbal 60 when suction is pulled on handle 12 using the pump mechanism. First gimbal joint seal includes an O-ring or gasket in some embodiments. First gimbal joint seal ensures that that any applied negative pressure from the pump mechanism in handle 12 is communicated and maintained through the interior port in gimbal 60 to suction head 14. Gimbal 60 may be secured to handle 12 using any suitable connection for allowing relative rotation between handle 12 and gimbal 60 about reference horizontal axis 17, and while preventing axial movement between handle 12 and gimbal 60 along reference horizontal axis. In some embodiments, handle 12 is attached to gimbal 60 using one or more mechanical fasteners such as bolts, set screws, clips or other suitable fasteners.

A second gimbal joint 64, shown in FIG. 2, provides a second angular degree of freedom, providing a pivoting joint between gimbal 60 and suction head 14. A second gimbal joint seal is disposed in second gimbal joint 64 to maintain a suction seal during rotation of gimbal 60 and handle 12 relative to suction head 14 while suction head 14 is engaged with a patient's skin. Thus, second gimbal joint 64 allows handle 12 to be rotated relative to suction head 14 about a reference vertical axis 19. Second gimbal joint seal may include any suitable seal such as but not limited to an O-ring or a gasket. Second gimbal joint seal maintains a sealing engagement between gimbal 60 and suction head 14 during rotation of handle 12 relative to suction head 14 and during application of suction force to the patient's tissue using suction head 14. Suction head 14 may be secured to gimbal 60 at second gimbal joint 64 in a number of different ways to provide relative sealed rotation between the structures about reference vertical axis 19. For example, in some embodiments, a horizontal U-shaped retaining pin may be installed in gimbal 60 to engage a corresponding stem groove in stem 40 on suction head 14. When the retaining pin is installed in the stem groove, the suction head 14 is secured in axial position relative to gimbal 60, thereby allowing gimbal 60 to rotate about reference vertical axis 19 relative to suction head 14, but preventing axial movement between suction head 14 and gimbal 60.

A vacuum gauge, or suction gauge 70, shown in FIG. 1, is disposed on gimbal 60 in some embodiments. Vacuum gauge 70 extends from gimbal along reference horizontal axis 17 in some embodiments. Vacuum gauge 70 is maintained in position along a gimbal port 66, shown in FIG. 4. Gimbal port 66 provides a passage through the gimbal for communicating pressure from pump 90 to suction head 14. Vacuum gauge 70 is disposed in an opening in communication with gimbal port 66, and a gauge spring 74 provides a spring force to maintain vacuum gauge 70 at an equilibrium position. When a reduced pressure is applied on suction head 14 through gimbal port 66, the pressure reduction causes vacuum gauge 70 to translate against gauge spring 74, retracting partially into the gimbal 60. One or more indicia 72 on vacuum gauge 70 provides information about a desired applied pressure level. For example, in some embodiments, indicia 72 includes a color band or a line indicating an acceptable applied pressure range for achieving a desired suction force on suction head 14. The pressure range corresponding to the indicia is a predetermined pressure range in some embodiments that has been calibrated to be a sufficient pressure to achieve a desirable suction force for lifting patient tissue using the device 10. When a corresponding pressure drop across gimbal port 66 is achieved, vacuum gauge 70 will retract such that the indicia 72 of a color band or line is aligned with vacuum gauge keeper 76, shown in FIG. 3. Alternatively, indicia 72 may be measured against another point of reference including any suitable structure on gimbal 60. The vacuum gauge 70 allows a user to visually determine when a desired negative pressure is achieved in suction head 14. Once the desired suction pressure is confirmed by visual observation of vacuum gauge 70, the user may then pull on handle 12 to lift the patient's tissue for insertion of a surgical instrument such as a trocar or Veress needle.

Referring further to FIG. 4, a pump 90 is disposed in handle 12 in some embodiments. Pump 90 includes a pump piston 80 that is moveable along the interior of handle 12. Handle 12 forms a pump piston cylinder 84 in some embodiments. During use, pump piston 80 translates along the pump piston cylinder 84 on the interior of handle 12. A pump piston seal 86 is positioned between pump piston 80 and pump piston cylinder 84. Pump piston seal 86 is a slidable seal such as an o-ring in some embodiments. Actuator 18 is linked to pump piston 80 such that translation of actuator 18 along travel slot 54 results in a corresponding motion of pump piston 80 along pump piston cylinder 84. Pump spring 82 presses against pump piston 80 and biases pump piston 80 in a position at the lower end of handle 12 toward suction head 14.

A spring stop 92 is installed on pump 90 inside handle 12. Spring stop 92 provides an axial stop for pump spring 82, which is a compression spring in some embodiments. Spring stop 92 also forms an end wall for pump piston cylinder 84. Spring stop 92 may be threaded into handle, secured in place using one or more fasteners, or fixed relative to handle 12 using any suitable fastening means such as but not including an adhesive or integrally molded into handle 12. Spring stop 92 also includes a spring pilot rod 94 extending axially downwardly toward suction head 14 in some embodiments. Spring pilot rod 94 includes a projecting rod positioned on the interior of pump spring 82, as shown in FIG. 4. Spring pilot rod 94 in some embodiments prevents pump spring 82 from buckling or becoming misaligned during spring compression that occurs during a stroke of pump 90.

During a procedure, a surgeon or assistant may grasp handle 12 and use a finger or thumb to move actuator 18 away from suction head 14, thereby causing pump piston 80 to translate away from suction head 14 along pump piston cylinder 84 inside handle 12. Such motion of pump piston 80 away from suction head 14 draws a negative pressure inside the pump piston cylinder 84. The negative pressure is maintained by pump piston seal 86. A corresponding negative pressure is also drawn through gimbal port 66, and through suction port 48 in suction head 14, causing a pressure drop in suction chamber 22. The negative pressure created by movement of actuator 18 creates a suction force on a patient's skin in suction chamber 22, thereby allowing a user to lift the patient's tissue for insertion of a surgical instrument such as a trocar or Veress needle.

In some applications, it may be necessary to initiate multiple pump strokes to achieve a desired suction pressure. For example, when actuator 18 is pulled to the end of its travel range, the pump spring 82 is operable to force the actuator and piston back toward the suction head 14. A pump valve 88 is included on pump piston 80 in some embodiments. Pump valve 88 is a check valve in some embodiments that is closed when pump piston 80 is drawn away from suction head 14, but is opened when pump piston 80 returns back toward suction head 14 to its starting position. The pump valve 88 allows the gas in pump piston cylinder 84 to vent out of the cylinder as the pump piston 80 returns via the pump spring 82.

Figure 5:
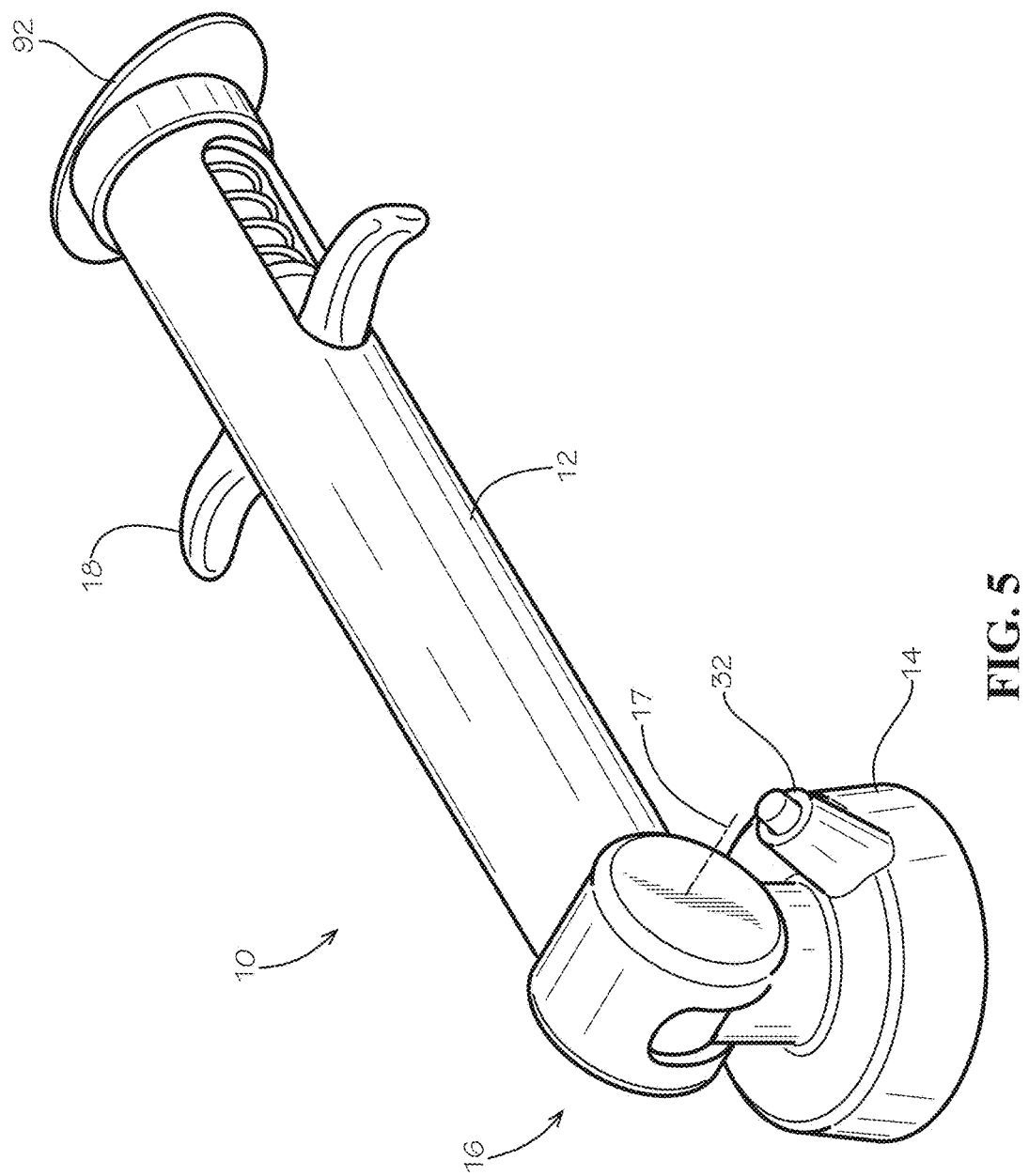
FIG. 5 is a perspective view of an alternative embodiment of a surgical device in accordance with the present disclosure.

In various alternative embodiments, different configurations of joint 16 and actuator 18 may be provided. Such alternative embodiments include a handle 12 and a suction head 14 configured for applying a suction force against a patient's skin. An example of an alternative embodiment of a surgical device 10 is shown in FIG. 5. The device 10 shown in FIG. 5 includes a center gimbal allowing for rotation about a reference horizontal reference axis 17 only. In this embodiment, the joint 16 includes only one angular degree of freedom. A spring stop 92 includes an adjustable end cap that may be axially adjusted relative to handle 12 by rotating the end cap in some embodiments. This allows a user to modify the axial grip length of the handle 12 for ergonomic purposes by adjusting the distance between the axial end cap and the actuator 18. The spring stop 92 including an adjustable end cap may also include an ergonomic shape such as an oval or hemisphere to comfortably fit in the palm of the user's hand. In some embodiments, the adjustable end cap is separate from the spring stop 92 housed within handle 12. In other embodiments, the adjustable end cap is integrally formed with the spring stop 92 as a single piece. Also shown in FIG. 5, an alternative embodiment of actuator 18 includes a single piece with opposing finger grips. The actuator 18 is inserted completely through handle 12 such that each opposing finger grip extends from an opposing side of handle 12. In other embodiments, each finger grip is a separate individual piece, as shown in FIG. 4.

Figure 6:
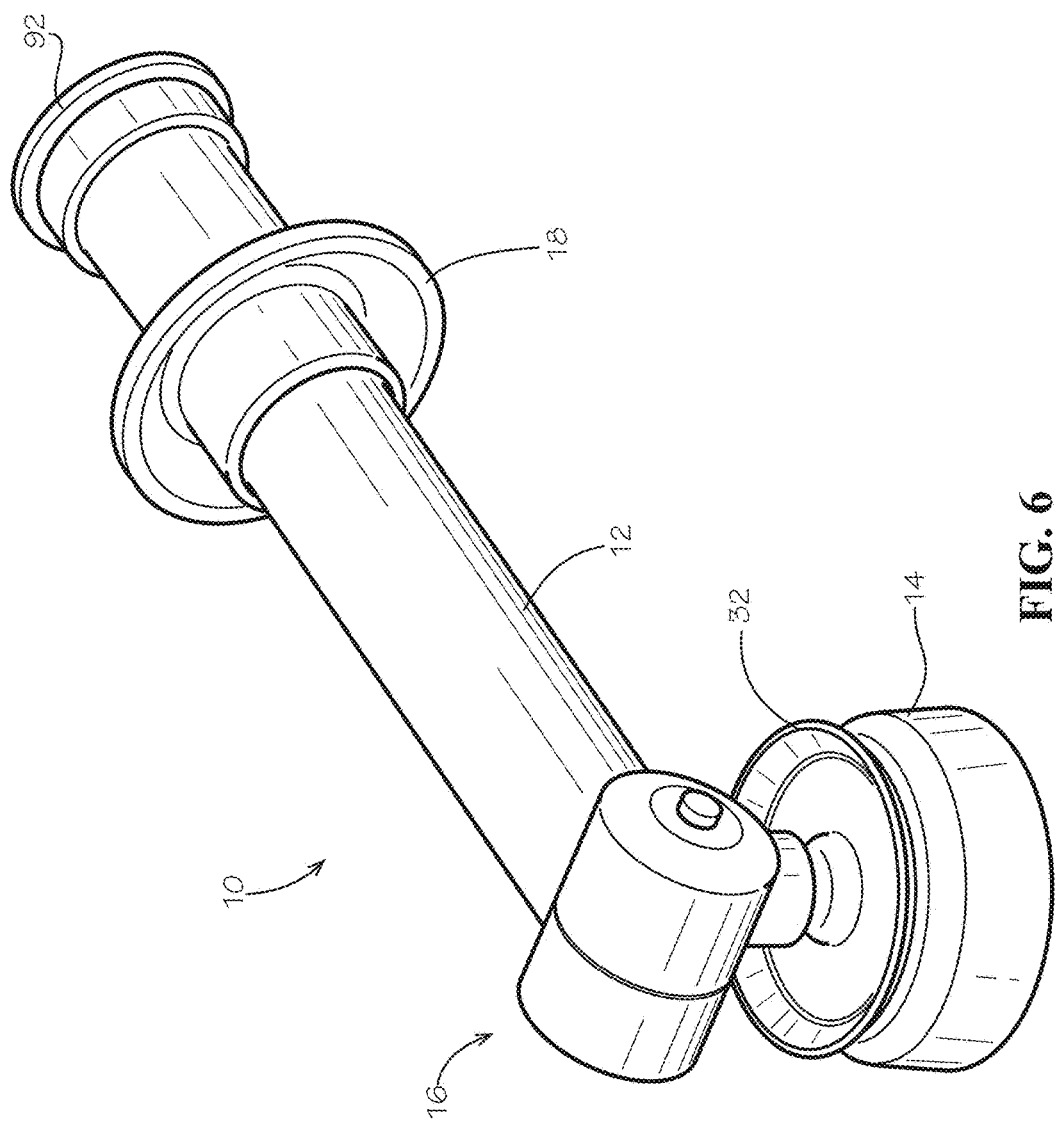
FIG. 6 is a perspective view of an alternative embodiment of a surgical device in accordance with the present disclosure.

Referring to FIG. 6, an alternative embodiment of a surgical device 10 is shown with a side gimbal design. In this embodiment, actuator 18 includes a continuous finger holder extending in a ring around handle 12. As shown in FIG. 6, this embodiment may also include a spring stop 92 forming an adjustable end cap that may be axially adjusted relative to handle 12 by rotating the end cap. Also shown in FIG. 5, pressure release 32 may take numerous forms to allow a release of negative pressure held inside suction chamber 22. In some alternative embodiments, as shown in FIG. 5, pressure release 32 includes a knob that may be released by turning, pressing or bending to open a seal on pressure release 32 to quickly release the suction drawn in suction chamber 22 against a patient's tissue.

Figure 7:
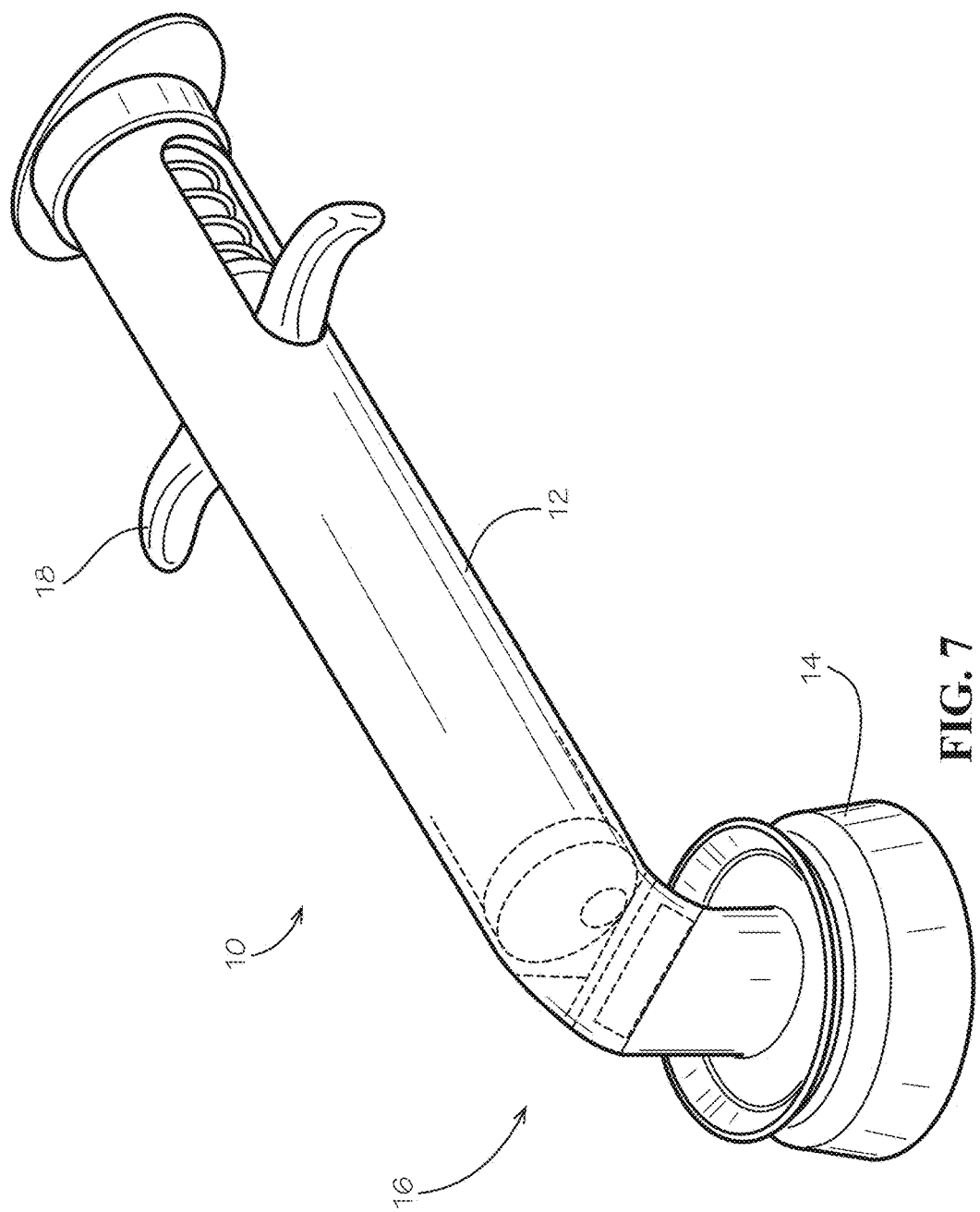
FIG. 7 is a perspective view of an alternative embodiment of a surgical device in accordance with the present disclosure.

Referring to FIG. 7, an alternative embodiment of a surgical device 10 includes a joint 16 having a bevel configuration. This configuration allows the handle 12 to be rotated relative to suction head 14 by turning about the beveled joint to achieve a desired orientation of handle relative to suction head 14.

Figure 8:
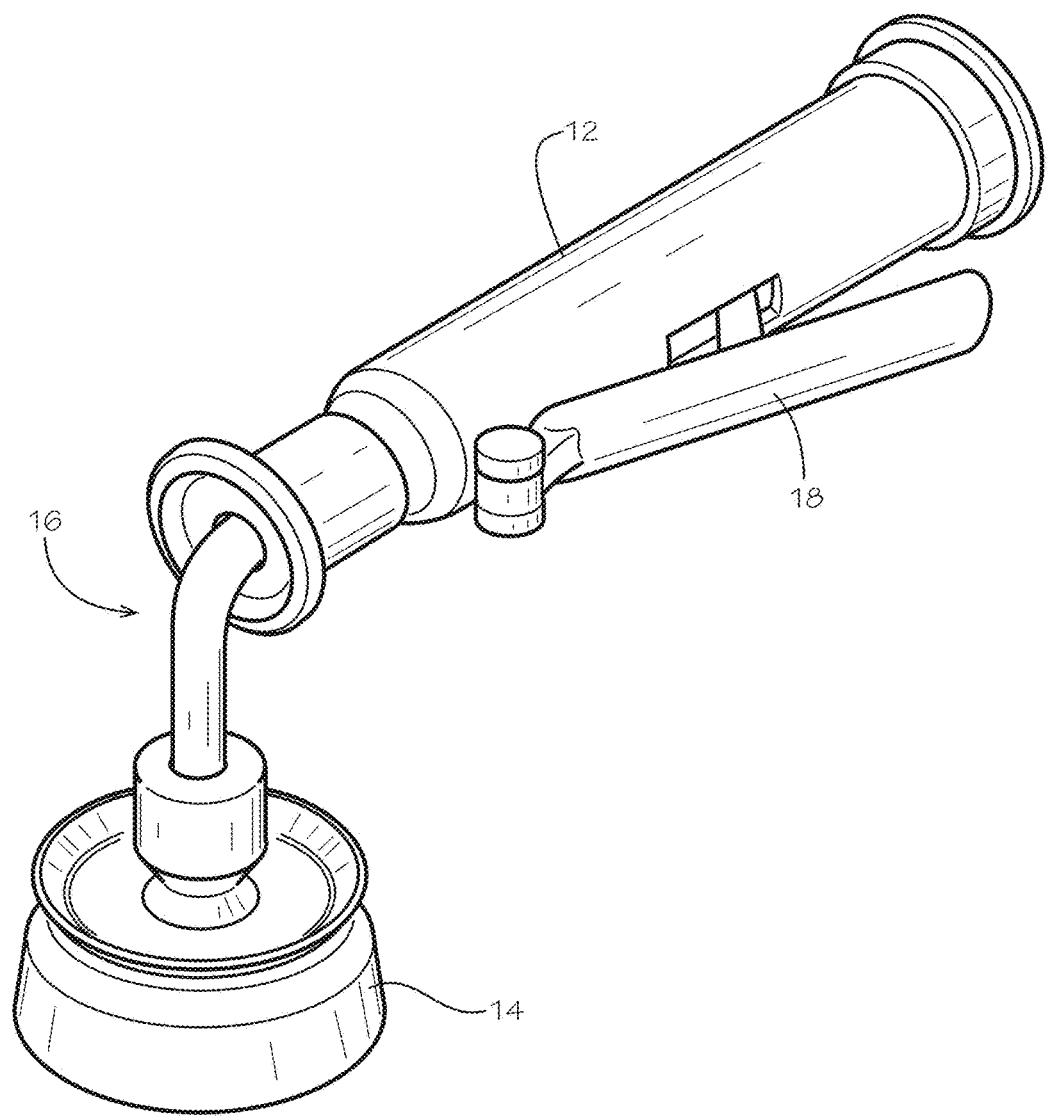
FIG. 8 is a perspective view of an alternative embodiment of a surgical device in accordance with the present disclosure.
Figure 9:
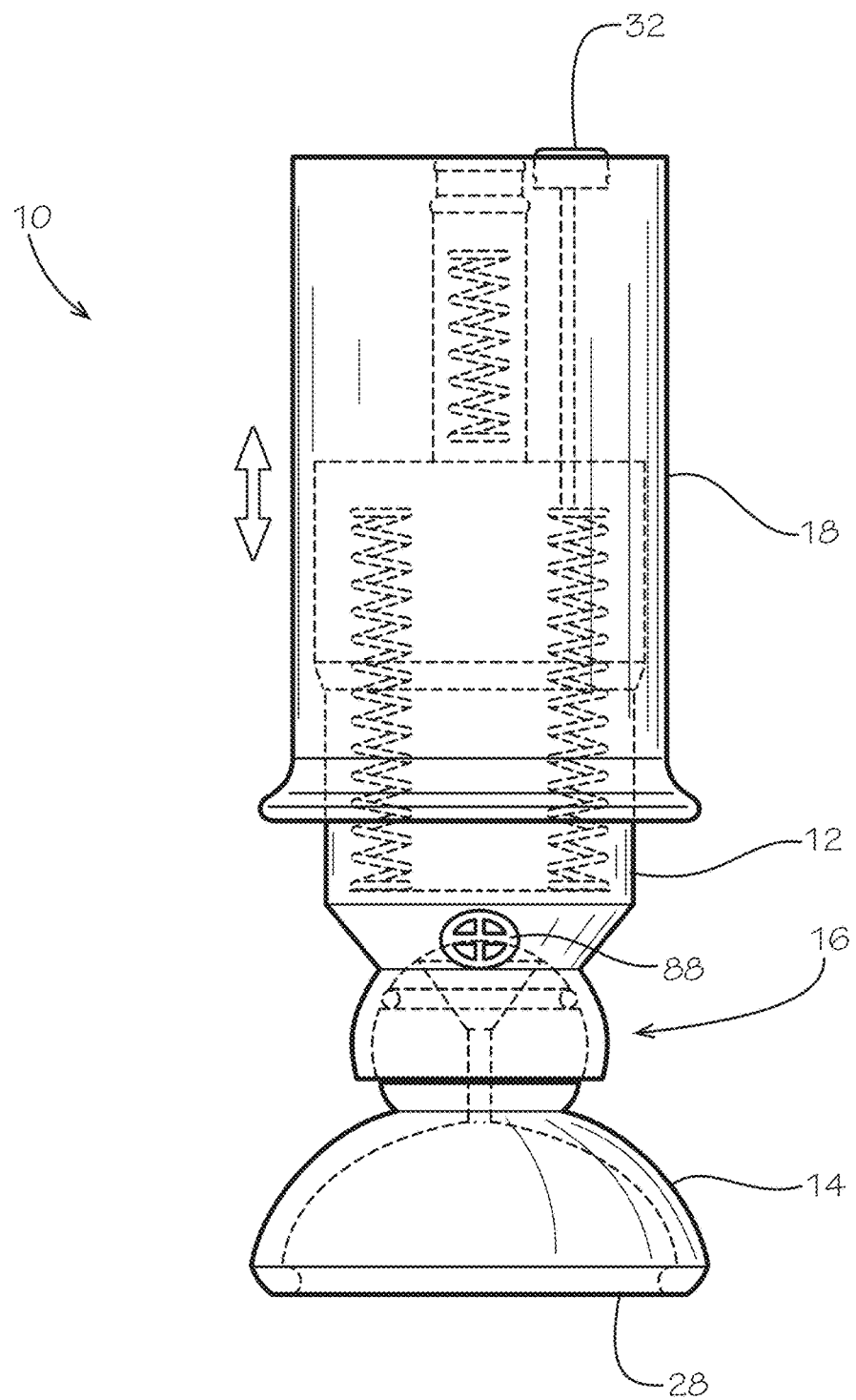
FIG. 9 is a front elevation view of an alternative embodiment of a surgical device in accordance with the present disclosure.
Figure 10:
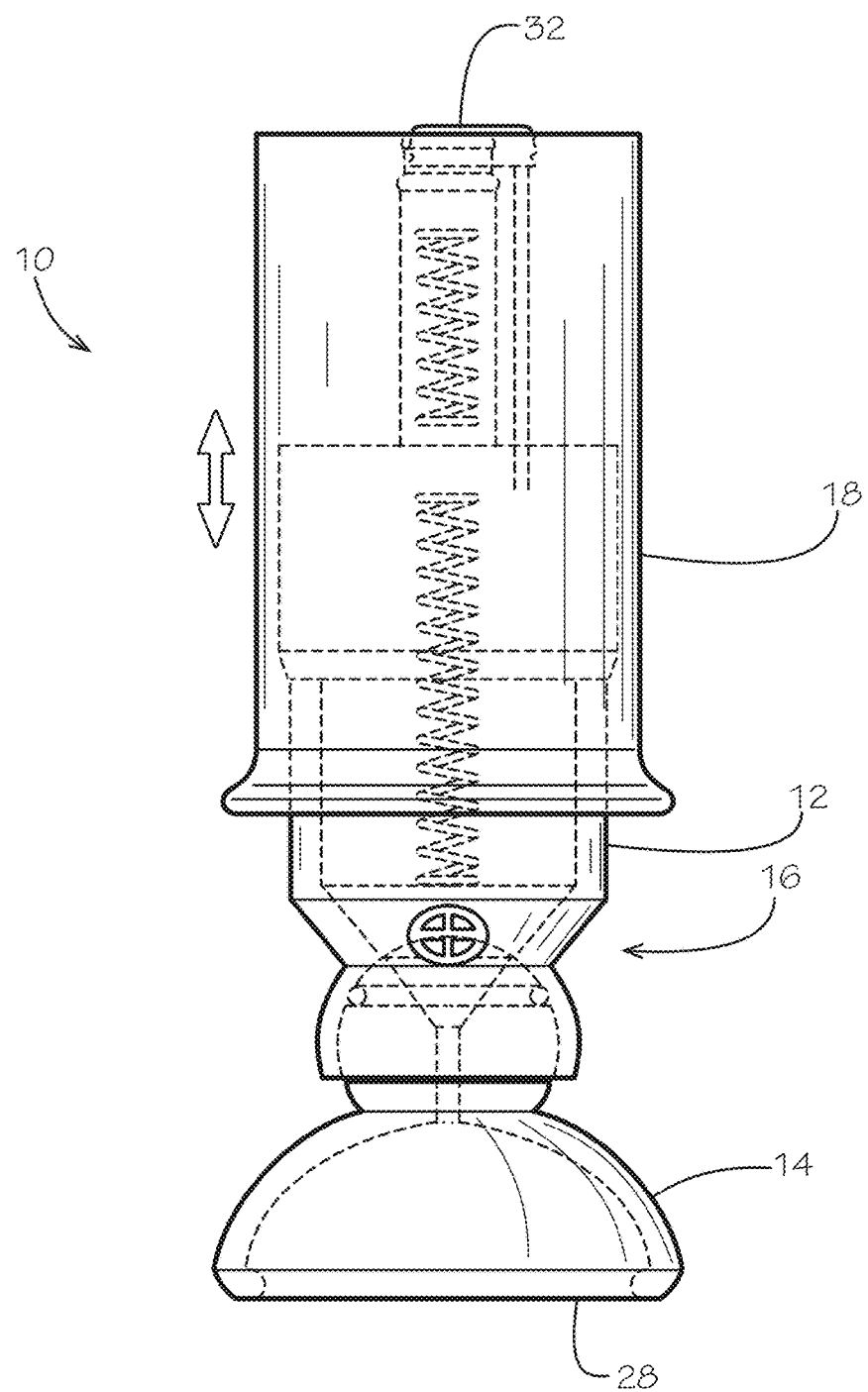
FIG. 10 is a side elevation view of an alternative embodiment of a surgical device in accordance with the present disclosure.

Referring to FIG. 8, an alternative embodiment of a surgical device 10 includes an actuator 18 having a pivotable lever on handle 12. When a user depresses the lever on actuator 18, the pump housed within handle 12 is stroked. Another feature shown in FIG. 8 is the use of a flexible medical tubing for the joint 16 between handle 12 and suction head 14. Flexible medical tubing may take the place of gimbal 60 in forming joint 16. The tubing allows at least two angular degrees of freedom between handle 12 and suction head 14, allowing handle to be pivoted relative to suction head 14 about reference horizontal axis 17 and also pivoted about reference vertical axis 19.

Figure 11:
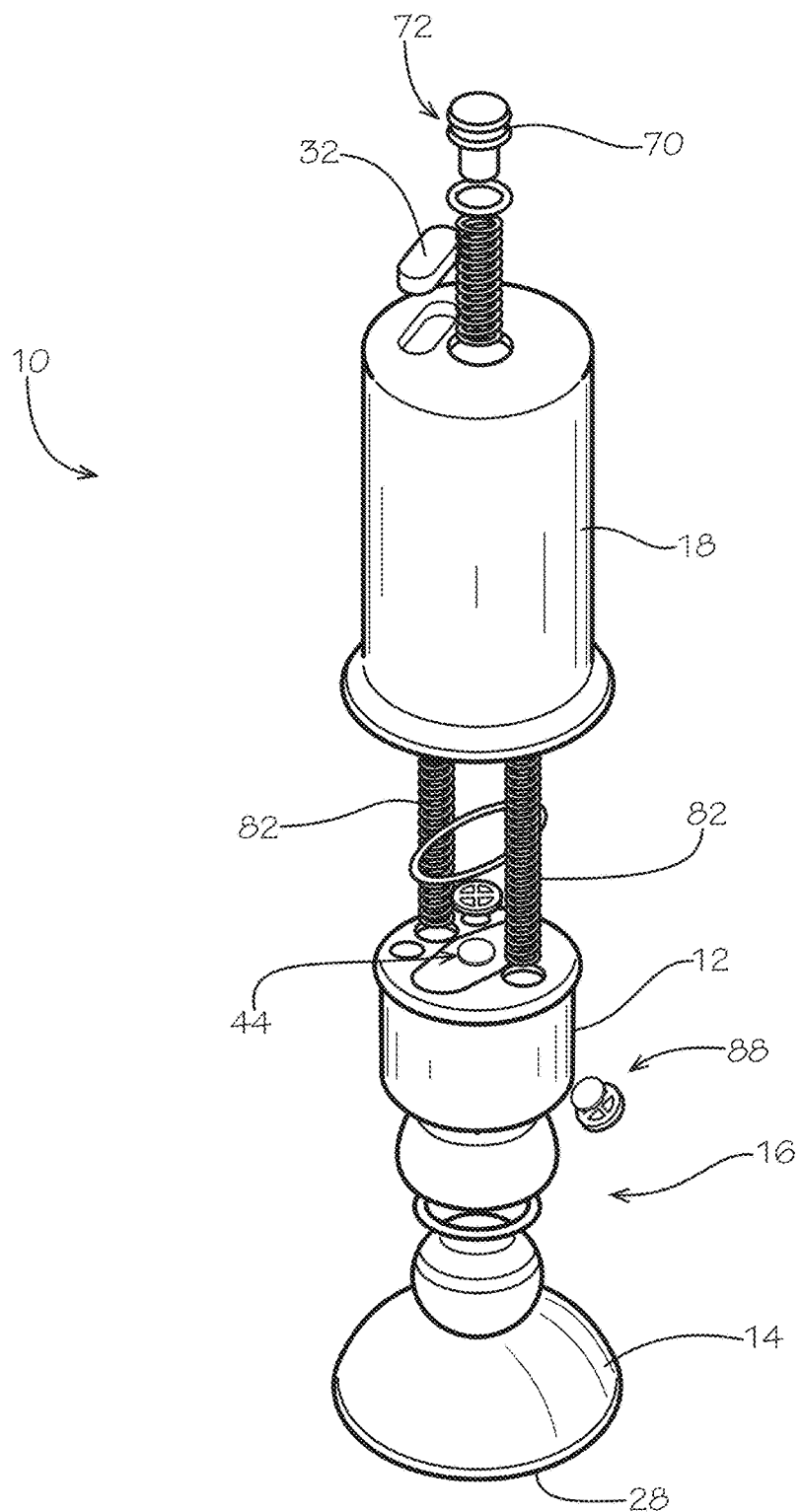
FIG. 11 is an exploded perspective view of an alternative embodiment of a surgical device in accordance with the present disclosure.
Figure 12:
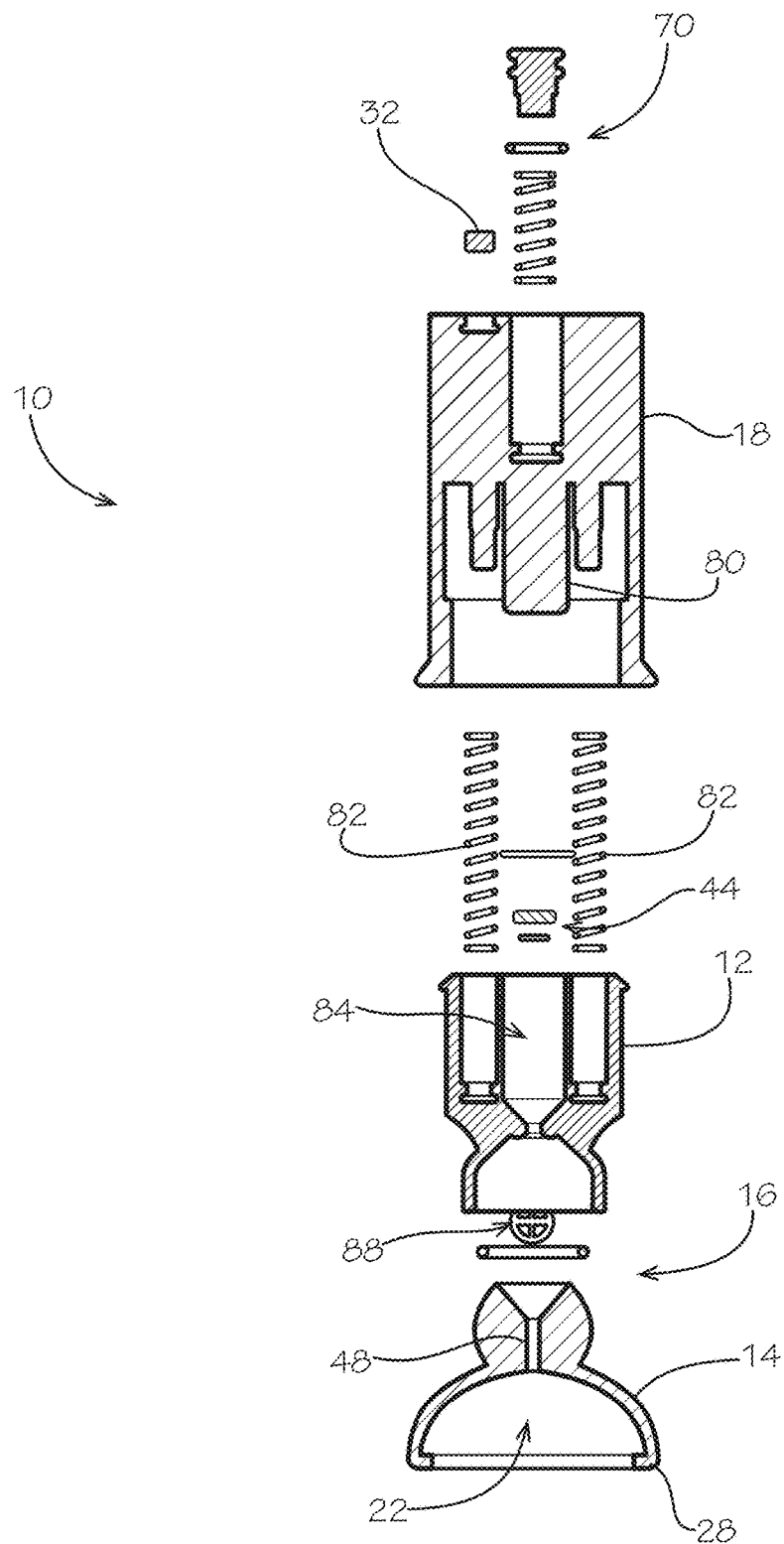
FIG. 12 is an exploded cross-sectional elevation view of an alternative embodiment of a surgical device in accordance with the present disclosure.

Referring to FIGS. 9-12, an alternative embodiment of a surgical device 10 is shown in a front view. The device 10 includes a handle 12 and a suction head 14. Handle 12 is secured to suction head 14 at an articulating joint 16. In some embodiments, joint 16 includes a ball and socket joint, including a ball on suction head 14 and a socket attached to handle 12. As shown in the alternative embodiment, a suction force may be applied in suction head 14 by using an axial stroking action of actuator 18 on handle 12. During use, an operator may grasp the actuator portion 18 on handle 12. Actuator 18 is moved up and down relative to handle 12 to actuate a pump housed on the interior of handle 12 and actuator 18. The upstroke motion of actuator 18 causes the pump to draw a vacuum inside suction chamber 22, shown in FIG. 12. A manual release 32, shown in FIG. 11, is positioned on actuator 18 to allow a user to quickly release the vacuum from suction chamber 22. First and second piston springs 82 provide an axial force to bias actuator 18 at its upward position. During use, the user presses actuator 18 down against piston springs 82, thereby moving a piston 80 on actuator 18 through a corresponding pump piston cylinder 84 defined in handle 12. When the actuator 18 is reversed and moved upward away from the suction head 14, a negative pressure is drawn as the actuator 18 moves the piston 80 upwardly through its pump piston cylinder 84 away from suction head 14. A suction valve 44 in the form of a check valve, shown in FIG. 11 and FIG. 12, maintains the negative pressure inside suction chamber 22 held in place by a seal between rim 28 and a patient's skin. Suction port 48, shown in FIG. 12, communicates the pressure drop associated with the motion of piston 80 from handle 12 to suction chamber 22 on suction head 14.

A pump valve 88 is included on handle 12 in some embodiments. Pump valve 88 is a check valve in some embodiments that is closed during the upstroke motion of actuator 18, but is opened when pump piston 80 is pressed downward through piston cylinder 84 toward suction head 14. The pump valve 88 allows the gas in pump piston cylinder 84 to vent out of the cylinder as it is pressed downward through piston cylinder 84 toward suction head 14.

The articulating joint 16 shown in some embodiments, such as the ball joint shown in FIGS. 9-12, provides at least two angular degrees of freedom between handle 12 and suction head 14. The ball and socket joint allows angular movement of handle 12 relative to suction head 14 about both a horizontal axis and a vertical axis.

Thus, although there have been described particular embodiments of the present invention of a new and useful device and method for lifting a patient's tissue for insertion of a surgical instrument such as but not limited to a trocar or Veress needle, it is not intended that such references to particular embodiments be construed as limitations upon the scope of this invention.

What is claimed is:

1. A surgical device apparatus, comprising:
   a handle;
   a pump disposed in the handle, the pump configured for drawing a negative pressure;
   an actuator disposed on the handle, the actuator linked to the pump;
   a suction head attached to the handle at an articulating joint, the suction head defining a suction chamber in fluid communication with the pump, wherein the pump is operable to communicate the negative pressure to the suction chamber; and
   a gimbal forming the joint between the handle and the suction head;
   wherein the joint includes at least one angular degree of freedom between the handle and the suction head.

2. The apparatus of claim 1, further comprising an actuator travel slot defined in the handle, wherein the actuator travels along the actuator travel slot when the pump is operated.

3. The apparatus of claim 2, further comprising a pump spring disposed in the handle.

4. The apparatus of claim 3, further comprising a pump piston disposed in the handle.

5. The apparatus of claim 4, wherein the pump spring biases the piston toward the suction head.

6. The apparatus of claim 5, wherein the interior of the handle forms a pump piston cylinder along which the pump piston may travel.

7. The apparatus of claim 6, wherein the actuator is linked to the pump piston and the pump piston moves in a direction away from the suction head when the actuator is moved in the same direction away from the suction head.

8. The apparatus of claim 7, further comprising a sliding pump piston seal between the pump piston and the pump piston cylinder in the handle.

9. The apparatus of claim 8, wherein the pump piston applies a negative pressure on the suction head when the actuator is moved in the direction away from the suction head.

10. The apparatus of claim 9, wherein the joint includes a second angular degree of freedom between the handle and the suction head.

11. The apparatus of claim 10, wherein the handle is pivotable relative to the gimbal about the horizontal reference axis.

12. The apparatus of claim 11, wherein the handle is pivotable relative to the gimbal about the vertical reference axis.

13. The apparatus of claim 12, further comprising a vacuum gauge disposed on the gimbal, the vacuum gauge including indicia representative of a predetermined pressure.

14. A surgical device apparatus for lifting a patient tissue for placement of a surgical instrument for a laparoscopic procedure, the apparatus comprising:

a handle forming a cylinder and a travel slot, the handle including an actuator moveable along the travel slot and a pump, the pump including a piston housed inside the cylinder in the handle, the actuator attached to the piston, wherein the actuator is moveable relative to the handle and wherein movement of the actuator relative to the handle causes the piston to travel in a corresponding motion inside the cylinder;

a gimbal pivotally disposed on the handle, the gimbal including a first angular degree of freedom wherein the handle may be rotated relative to the gimbal about a horizontal reference axis;

a suction head disposed on the gimbal, the suction head including a suction chamber having a rim positioned for engagement with the patient's skin, the gimbal including a second angular degree of freedom wherein the gimbal may be rotated relative to the suction head about a vertical reference axis; and a pressure release disposed on the suction head.

15. The apparatus of claim 14, further comprising a vacuum gauge disposed on the gimbal, the vacuum gauge including indicia representative of a predetermined pressure.

* * * * *